(12) United States Patent
Poore et al.

(10) Patent No.: US 9,937,064 B2
(45) Date of Patent: Apr. 10, 2018

(54) OSSEOINTEGRATED NEURAL INTERFACE AND METHOD

(71) Applicant: Wisconsin Alumni Research Foundation, Madison, WI (US)

(72) Inventors: Samuel O. Poore, Madison, WI (US); Justin C. Williams, Cambridge, WI (US); Sarah K. Brodnick, Middleton, WI (US); Thomas J. Richner, Middleton, WI (US); Sahil K. Kapur, Fitchburg, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 40 days.

(21) Appl. No.: 15/049,297

(22) Filed: Feb. 22, 2016

(65) Prior Publication Data

US 2017/0239069 A1 Aug. 24, 2017

(51) Int. Cl.
*A61F 2/72* (2006.01)
*A61F 2/28* (2006.01)
*A61F 2/78* (2006.01)
*A61B 5/04* (2006.01)
*A61B 5/00* (2006.01)
(Continued)

(52) U.S. Cl.
CPC ............ *A61F 2/72* (2013.01); *A61B 5/04001* (2013.01); *A61B 5/04888* (2013.01); *A61B 5/4851* (2013.01); *A61F 2/2814* (2013.01); *A61N 1/0551* (2013.01); *A61N 1/36135* (2013.01); *A61F 2002/6827* (2013.01); *A61F 2002/7887* (2013.01); *A61F 2250/0002* (2013.01)

(58) Field of Classification Search
CPC .. A61F 2/2814; A61F 2/72; A61F 2002/7887; A61B 5/04888; A61B 5/4851

USPC ..................................................... 623/25, 32
See application file for complete search history.

(56) References Cited

U.S. PATENT DOCUMENTS

| 7,302,296 | B1 * | 11/2007 | Hoffer ....................... A61F 2/72 607/46 |
| 9,067,057 | B2 * | 6/2015 | Branemark ............... A61N 1/05 |
| 2013/0253606 | A1 * | 9/2013 | Youn ................... A61N 1/36003 607/48 |

OTHER PUBLICATIONS

Boldrey, E., "Amputation Neuroma in Nerves Implated in Bone", Ann Surg 1943, 118, 1052-7.
(Continued)

*Primary Examiner* — David H Willse
(74) *Attorney, Agent, or Firm* — Boyle Fredrickson, S.C.

(57) ABSTRACT

An osseointegrated neural interface (ONI) is provided for control of a prosthetic. The ONI includes an elongated, hollow rod having a first end receivable in an intramedullary cavity of a bone, a second end operatively connected to the prosthetic and an inner surface defining a cavity. An electrode is receiveable on a terminal end of a peripheral nerve and positionable within the cavity of the rod. The electrode being capable of sensing the neural signals generated by the peripheral nerve and stimulating the peripheral nerve. A recording/stimulation unit, receiveable within the cavity of the rod, records the neural signals from the peripheral nerve sensed by the electrode and transmits the signals to a controller operatively connected thereto. The controller controls operation of the prosthetic in response to the neural signals recorded by the recording unit. In addition, the controller receives stimulation signals from a sensor in the prosthetic and causes the electrode to stimulate the peripheral nerve via the recording/stimulation unit in response thereto.

33 Claims, 3 Drawing Sheets

(51) Int. Cl.
    A61N 1/05      (2006.01)
    A61N 1/36      (2006.01)
    A61B 5/0488    (2006.01)
    A61F 2/68      (2006.01)

(56) References Cited

OTHER PUBLICATIONS

Branemark et al., "A novel osseointegrated percutaneous prosthetic system for the treatment of patients with transfemoral amputation", The Bone & Joint Journal, 2014; 96-B(1):106-13.

Campbell, WW, "Evaluation and management of peripheral nerve injury", Clinical Neurophysiology 119 (2008) 1951-1965.

Hemmy, DC, "Intramedullary nerve implantation in amputation and other traumatic neuromas", J. Neurosurg. 54:842-843, 1981.

Jeyapalina et al., "Radiographic Evaluation of Bone Adaptation Adjacent to Percutaneous Osseointegrated Prostheses in a Sheep Model", Clin Orthop Relat Res (2014) 472:2966-2977.

Kung et al., "Innovations in Prosthetic Interfaces for the Upper Extremity", Plastic and Reconstructive Surgery 2013, 132, 1515-23.

Maricevic et al., "War Injuries to the Extremities", Military Medicine, 162, 12:808-11, 1997.

Mass et al.; "Treatment of Painful Hand Neuromas by Their Transfer into Bone", 1984, Plast. Reconstr. Surg. 74, 182-5.

Panetsos et al., "Neural Prostheses: Electrophysiological and Histological Evaluation of Central Nervous System Alterations Due to Long-Term Implants of Sieve Electrodes to Peripheral Nerves in Cats", IEE Transactions on Neural Systems and Rehabilitation Engineering, vol. 16, No. 3, Jun. 2008, 223-32.

Pearce et al., "Animal Models for Implant Biomaterial Research in Bone: A Review", European Cells and Materials, vol. 13, 2007, 1-10.

Peramo et al., "In Situ Polymerization of a Conducive Polymer in Acellular Muscle Tissue Constructs", Tissue Engineering: Part A, vol. 14, No. 3, 2008, 423-32.

Schultz et al., "Neural Interfaces for Control of of Upper Limb Prostheses: The State of the Art and Future Possibilities", PM&R, vol. 3. Jan. 2011, 55-67.

Sullivan et al., "Rehabilitation of the trans-femoral amputee with an osseointegrated prosthesis: the United Kingdom experience", Prosthetics and Orthotics International, 2003, 27, 114-120.

Van de Meent et al., "Walking Ability and Quality of Life in Subjects With Transfemoral Amputation: A Comparison of Osseointegration With Socket Prostheses", Archives of Physical Medicine and Rehabilitation 2013; 94:2174-8.

* cited by examiner

OSSEOINTEGRATED NEURAL INTERFACE AND METHOD

REFERENCE TO GOVERNMENT GRANT

This invention was made with government support under N66001-12-C-4025 awarded by the U.S. Navy. The government has certain rights in the invention.

FIELD OF THE INVENTION

This invention relates generally to the control of prosthetics, and in particular, to an osseointegrated neural interface for interconnecting a peripheral nerve to a prosthetic for controlling the same and a method.

BACKGROUND AND SUMMARY OF THE INVENTION

Peripheral nerves interconnect an individual's central nervous system (CNS) to the other parts of their body, such as limbs, organs and muscles. Unfortunately, peripheral nerve injuries are common, often resulting from trauma or surgical complications. Further, the incidence of peripheral nerve trauma in the military population is increasing and approximately 5 to 10 times greater than in the civilian population. Pathology in this population is caused mainly due to shrapnel from blast events. With the advent of improved core body armor, such as that used in recent military action in the Middle East, the ratio of injuries resulting in wounds rather than death has doubled. This translates into a much higher rate of peripheral trauma, peripheral nerve injury, and amputations.

It can be appreciated that peripheral nerve injuries impose a number of adverse health conditions or disabilities on their victims. These adverse health conditions and disabilities place significant physical and economic burdens on the victims. In addition, these burdens are often shared by the victim's family, community and workplace. Further, adverse health conditions and disabilities resulting from peripheral nerve injuries place significant economic burdens on the health care system and on the economy in general. Considerable amounts of money, time and effort have been expended on various attempts to lessen, prevent or ameliorate the effects of trauma on peripheral nerves.

Despite significant advancements in composite tissue allotransplantion, allowing for upper extremity transplant below the elbow, problems remain with long-term allograft stability secondary to rejection, as well as, with nerve regeneration over long distances. Specific to lower extremity amputation, minimal progress has been made in composite tissue allotransplantation. Thus, the use of prosthetic limbs remains the gold standard for replacing amputated extremities.

In the past several decades, remarkable advancements have been made in the engineering of prosthetic limbs. These improvements include the development of implantable myoelectric interfaces that harness electromyographic data to control prostheses. The regenerative peripheral nerve interface (RPNI) is one such interface that is comprised of a free muscle unit neurotized with a peripheral nerve of interest. Other groups have developed recording interfaces by redirecting nerves from amputated stumps to reinnervate healthy adjacent muscles (Targeted Muscle Reinnervation). In these strategies, the neural interface is primarily composed of soft tissue elements and, in essence, is subject to a high degree of motion artifact. Any connection, whether wired or wireless, between the recording electrodes and the receiver on a prosthesis will be subject to unpredictable motion and/or strain in an actively moving subject.

Therefore, it is a primary object and feature of the present invention to provide osseointegrated neural interface for interconnecting a prosthetic to a peripheral nerve.

It is a further object and feature of the present invention to provide osseointegrated neural interface for interconnecting a prosthetic to a peripheral nerve wherein the peripheral nerves (e.g. sciatic or median) is redirected into an intramedullary canal of long-bone (e.g. humerus, femur) after amputation.

It is a further object and feature of the present invention to provide osseointegrated neural interface for interconnecting a prosthetic to a peripheral nerve wherein a hollow core rod defines an implant platform which includes various perforations and circuitry necessary to transmit recorded signals from electrodes operatively connected to the peripheral nerve to the prosthetic or provide electrical stimulation to the peripheral nerve.

It is a further object and feature of the present invention to provide osseointegrated neural interface for interconnecting a prosthetic to a peripheral nerve which includes electrode arrays connected to circuitry within hollow core implant platform.

It is a further object and feature of the present invention to provide an osseointegrated neural interface for interconnecting a prosthetic to a peripheral nerve including an implant platform positionable in an intramedullary canal of a long-bone (e.g., humerus, femur) and allowing for passage of a nerve sprout through fenestrations in the implant platform.

It is a further object and feature of the present invention to provide an osseointegrated neural interface for interconnecting a prosthetic to a peripheral nerve including thin flexible electrode arrays (cuff and/or sieve) that are integrated within an implant platform for interfacing a peripheral nerve of interest using microsurgical techniques.

It is a still further object and feature of the present invention to provide an osseointegrated neural interface for interconnecting a prosthetic to a peripheral nerve including an anchor for interconnecting a nerve stump to a long-bone that is stable and immobile.

In accordance with the present invention, an osseointegrated neural interface (ONI) for control of a prosthetic is provided. The osseointegrated neural interface includes an elongated, hollow rod having a first end receiveable in an intramedullary cavity of a bone, a second end operatively connected to the prosthetic and an inner surface defining a cavity. An electrode is receiveable on a terminal end of a peripheral nerve and positionable within the cavity of the rod. The electrode senses the neural signals generated by the peripheral nerve.

An anchor is extendable about peripheral nerve and is receiveable in an opening in the bone. The anchor secures the peripheral nerve to the bone. The electrode includes a plurality of openings therethrough. The plurality of openings are adapted for allowing the passage of nerve sprouts from the peripheral nerve therethrough. The rod includes a plurality of fenestrations extending therethrough. The plurality of fenestrations are adapted for allowing the passage of nerve sprouts from the peripheral nerve therethrough. The electrode may include a base and a plurality of spikes projecting therefrom. The spikes sense the neural signals generated by the peripheral nerve and/or also stimulate the peripheral nerve.

The electrode is operatively connected to a recording unit and/or a stimulation unit. The recording unit recording the neural signals from the peripheral nerve sensed by the electrode. The recording unit may be receivable within the cavity of the rod. A controller is operatively connected to the recording unit. The controller controls operation of the prosthetic in response to the neural signals recorded by the recording unit. In addition, it is contemplated for the controller to send electrical stimulation pulses to the peripheral nerve based on information received from various additional sensors provided in the prosthetic (e.g., pressure, temperature, position, etc). These sensors are meant to recapitulate the natural sensations perceived by the normal limb.

In accordance with a further aspect of the present invention, a method is provided of controlling a prosthetic. The method includes the step of positioning a first end of an elongated, hollow rod within an intramedullary cavity of a bone. The rod has an inner surface defining a cavity. A second end of the rod is interconnected to the prosthetic. A terminal end of a peripheral nerve is positioned within the cavity of the rod. The neural signals generated by the peripheral nerve are monitored and movement of the prosthetic is controlled in response to the neural signals monitored.

The peripheral nerve may be anchored to the bone and an electrode may be positioned on a terminal end of the peripheral nerve. The electrode senses the neural signals generated by the peripheral nerve. The electrode is configured to allow nerve sprouts extending from the peripheral nerve to pass therethrough and the rod is configured to allow the nerve sprouts extending from the peripheral nerve to pass therethrough. The rod includes a plurality of fenestrations extending therethrough. The plurality of fenestrations is adapted for allowing the passage of nerve sprouts from the peripheral nerve therethrough. The fenestrations may also define locations for annular electrodes. The annular electrodes may surround the fenestrations so as to make intimate contact with nerve processes that sprout through the fenestrations.

Movement of the prosthetic is controlled in response to the neural signals monitored by positioning an electrode about the peripheral nerve. The neural signals from the peripheral nerve sensed by the electrode are recorded. Operation of the prosthetic is controlled in response to the neural signals recorded. The recording unit is positioned in the cavity in the rod and operatively connected to the electrode. A controller is positioned in the prosthetic. The controller is configured to control operation of the prosthetic in response to the neural signals recorded by the recording unit and/or to control operation through receiving sensed inputs from various sensors within the prosthetic and stimulate the peripheral nerve accordingly. The controller is operatively connected to the recording unit to receive the neural signals recorded by the recording unit and/or to a stimulating unit to stimulate nerves to provide artificial sensation of the prosthetic.

BRIEF DESCRIPTION OF THE DRAWINGS

The drawings furnished herewith illustrate a preferred construction of the present invention in which the above advantages and features are clearly disclosed as well as other which will be readily understood from the following description of the illustrated embodiment.

In the drawings.

DETAILED DESCRIPTION OF THE DRAWINGS

Figure 1:
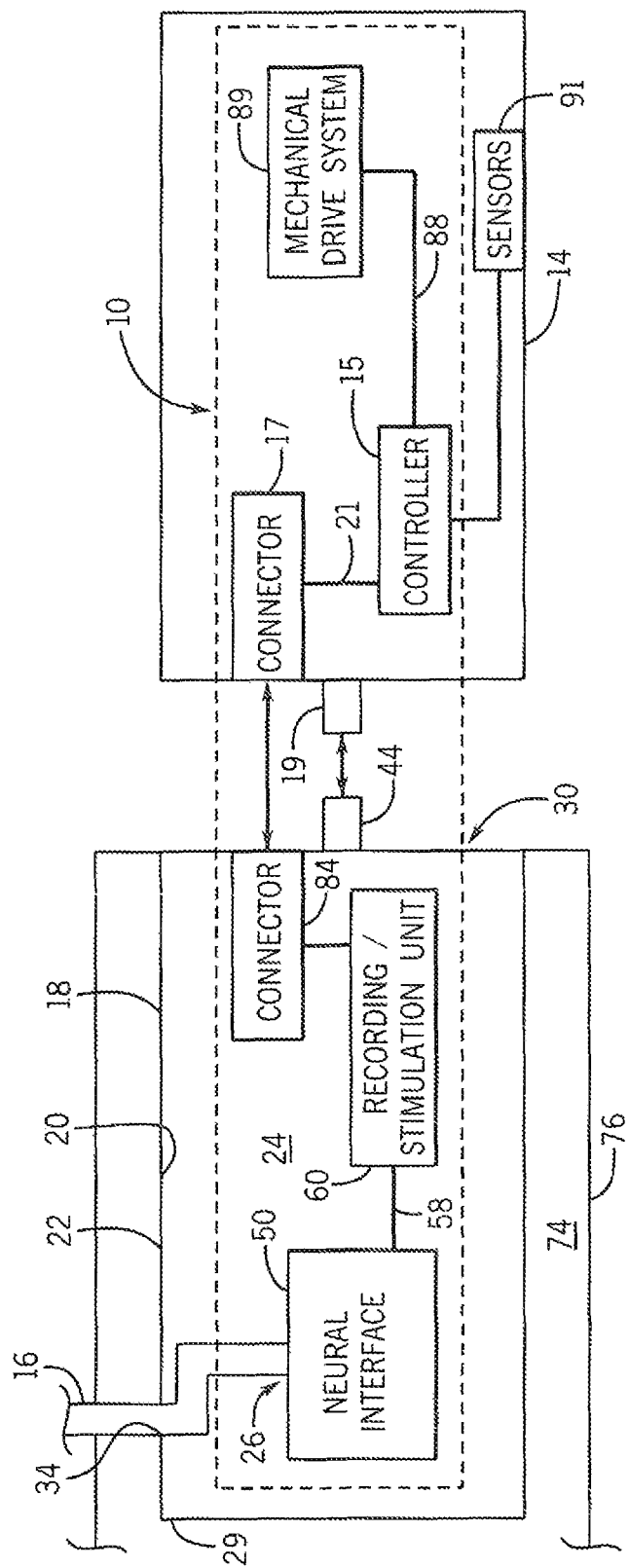
FIG. 1 is a schematic view of an osseointegrated neural interface in accordance with the present invention interconnecting a peripheral nerve to a prosthetic.
Figure 2:
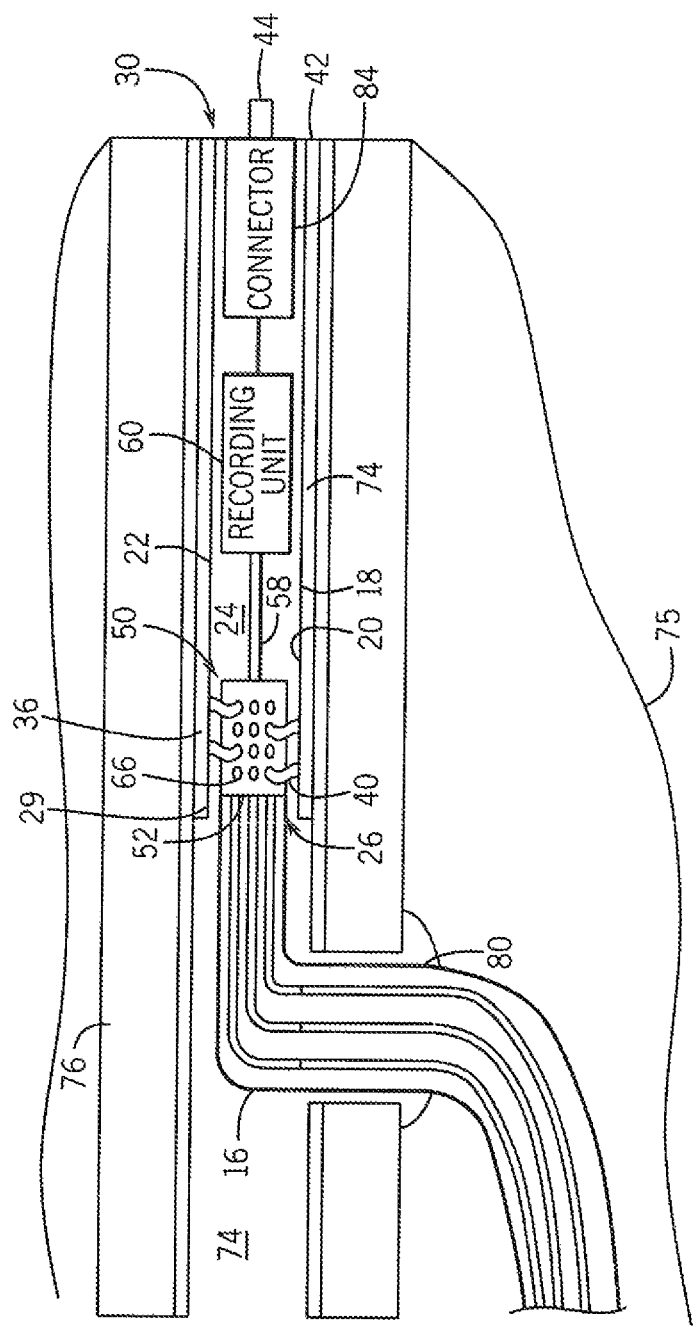
FIG. 2 is a schematic view of a portion of the osseointegrated neural interface of FIG. 1 received in a amputated stump

Referring to FIGS. 1-2, an osseointegrated neural interface (ONI) in accordance with the present invention, is generally designated by the reference numeral 10. It is intended for ONI 10 to provide a direct structural connection between a living bone (e.g. long bone 76) and prosthetic 14 and a functional connection between peripheral nerve 16 and prosthetic 14. It is contemplated for prosthetic 14 to house controller 15 which controls movement and operation of prosthetic 14 in response to nerve impulse signals received from peripheral nerve 16, as hereinafter described. Alternatively, controller 15 may be housed within the interior of rod 18, hereinafter described, or intramedullary canal 74 of long bone 76, without deviating from the scope of the present invention. In addition, it is contemplated for the controller 15 to provide stimulation to peripheral nerve 16 in response to sensor input from the prosthetic. It is contemplated for such stimulation to take the form of electrical stimulation, as hereinafter described. However, other forms of stimulation, such as optical stimulation, are contemplated as being within the scope of the present invention.

Prosthetic 14 further includes a connection member 19 for interconnecting prosthetic 14 to a conventional prosthetic coupling provided at the terminal end of an amputated stump. The input to controller 15 is operatively connected by line 21 to a connector 17 to facilitate the receipt of the nerve impulse signals, as hereinafter described. While line 21 is depicted as a physical connection, it can be appreciated that line 21 may take the form of an RF link, an optical link, an inductive link, or any other data linkage known in the art, without deviating from the scope of the present invention.

ONI 10 includes an elongated tubular rod 18, preferably fabricated from titanium. However, rod 18 may be fabricated from other materials without deviating from the scope of the present invention. Rod 18 extends along a longitudinal axis and is defined by inner and outer surfaces 20 and 22, respectively. Inner surface 20 of rod 18 defines a cavity 24 for receiving terminal end 26 of peripheral nerve 16 therein, as hereinafter described. Rod 18 further includes first and second opposite ends 29 and 30, respectively. First end 29 of rod 18 defines an opening 32, FIG. 2, therein for allowing peripheral nerve 16 to be inserted into cavity 24 of rod 18. Alternatively, an opening 34 may be provided in rod 18 between the inner and outer surfaces 20 and 22, respectively, at a desired location to allow peripheral nerve 16 to be inserted into cavity 24 of rod 18, FIG. 1.

Figure 7:
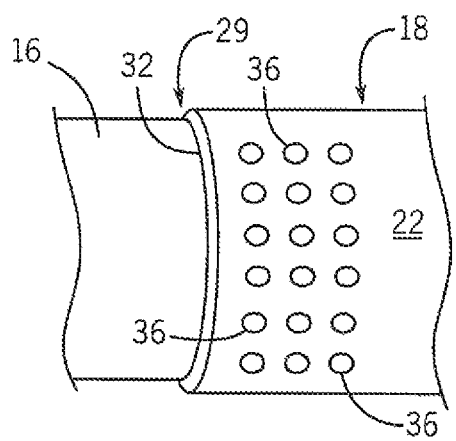
FIG. 7 is an isometric view showing a first end of a peripheral nerve received in a first end of a rod for use with the osseointegrated neural interface of the present invention.

As best seen in FIGS. 2 and 7, a plurality of fenestrations 36 extend through in rod 18 between the inner and outer surfaces 20 and 22, respectively, thereof at a location adjacent opening 32 (or opening 34 in FIG. 1) in rod 18. The plurality of fenestrations 36 are configured to allow for the passage of nerve sprouts 40 extending from peripheral nerve 16, as hereinafter described. Second end 30 of rod 18 defines an opening 42 adapted for connecting rod 18 to prosthetic coupling 44. By way example, inner surface 20 of rod 18 may include threads adjacent second end 30 thereof which are adapted for receiving mating threads provided on prosthetic coupling 44.

Figure 3:
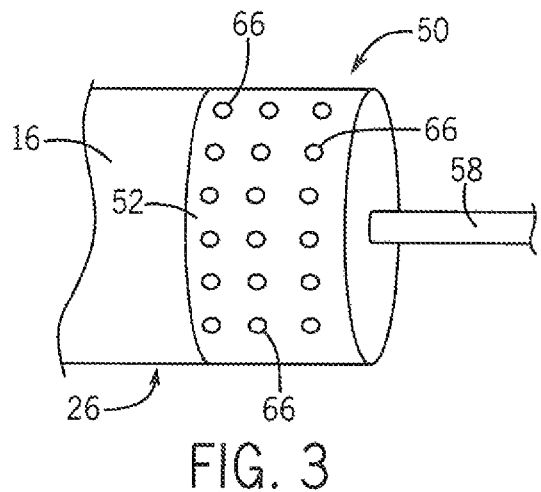
FIG. 3 is an isometric view of a first embodiment of a neural interface for use with the osseointegrated neural interface of the present invention.

ONI 10 further includes a nerve interface 50 adapted for receipt on terminal end 26 of peripheral nerve 16, FIGS. 1-2. Nerve interface 50 includes pad 52 formed from biocompatible polymers, FIGS. 3-6. Pad 52 may have a generally tubular configuration, FIG. 3, so as to allow nerve interface to be slid over terminal end 26 of peripheral nerve 16 or have a generally flat configuration, FIG. 4, wherein pad 52 is wrapped around terminal end 26 of peripheral nerve 16. It is contemplated for the surface chemistry of pad 52 to allow for a host of bioactive organic species to be either absorbed or covelantly bonded to the surfaces thereof. Alternatively, pad 52 may include three-dimensional (3D) biomaterial scaffolds, microfabricated set of tubes made of bio-inductive materials or living cells that coat the surfaces of pad 52 and/or fill the plurality of fenestrations 36 and/or cavity 24 in rod 18. The bioactivity of pad 52 is intended to provide an optimal implant environment and maximize the ability of pad 52 to be maintained on terminal end 26 of peripheral nerve 16 without inducing excessive foreign body or immune response.

Pad 52 may include a plurality of apertures 66 to allow for the passage of nerve sprouts 40 extending from peripheral nerve 16 therethrough, as hereinafter described. Inner surface 54 of pad 52 includes a plurality of electrodes 56 having corresponding wire traces 58 extending therefrom. It can be appreciated that apertures 66 increase the porosity of pad 52, and as such, increase the biocompatibility between nerve interface 50 and peripheral nerve 16. Further, it can be appreciated that chemicals, drugs or other stimuli may be provided within apertures 66 of nerve interface 50 to further enhance the biocompatibility of nerve interface 50 and peripheral nerve 16 and/or to apply various treatments to peripheral nerve 16. Alternatively, it is contemplated for these chemical treatments to induce the guidance of nerve sprouts 40, such as sensory or motor nerve subtypes, selectively towards parts of the osseointegrated neural interface or towards selective electrodes 56.

Figure 4:
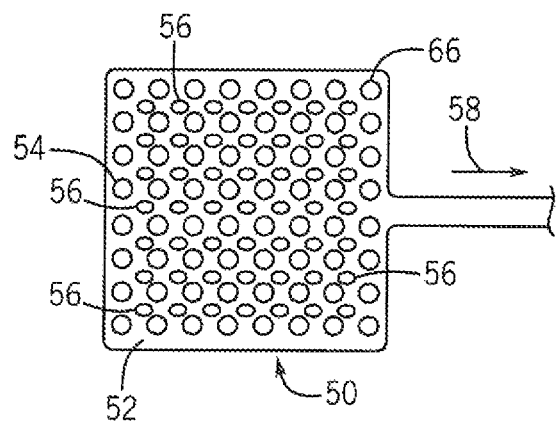
FIG. 4 is a top plan view of a second embodiment of a neural interface for use with the osseointegrated neural interface of the present invention.
Figure 5:
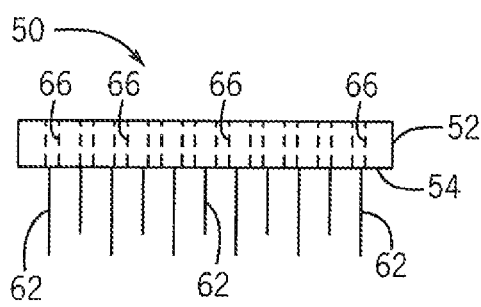
FIG. 5 is a side elevational view of a third embodiment of a neural interface for use with the osseointegrated neural interface of the present invention.
Figure 6:
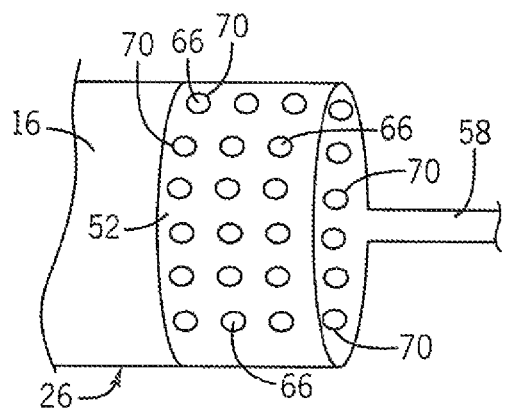
FIG. 6 is an isometric view of a fourth embodiment of a neural interface for use with the osseointegrated neural interface of the present invention.

Electrodes 56 along inner surface 54 of pad 52 may take the form of generally flat electrodes arranged in any suitable pattern, e.g. in designated rows and columns, FIG. 4. Electrodes 56 are intended to sense nerve impulses generated by peripheral nerve 16 or stimulate neuron activity, for reasons hereinafter described. It can be appreciated that other configurations of electrodes 56 are contemplated as being within the scope of the present invention. By way of example, the electrodes may take the form of spike electrodes 62 projecting from inner surface 54 of pad 52, FIG. 5. Spike electrodes 62 may have varying lengths so as to sense nerve impulses from a variety of depths within peripheral nerve 16 on which neural interface 50 is received. Alternatively, it is contemplated for sieve electrodes 70 to define the plurality of apertures 66 extending through pad 52 to sense nerve impulses generated from or to stimulate nerve sprouts 40 extending from peripheral nerve 16 and passing therethough, FIG. 6. Each wire trace 58 has a first end integral with a corresponding electrode 56, 62 or 70 and a second end operatively connected to a recording/stimulation unit 60, for reasons hereinafter described. It is further contemplated to provide first and second electrodes about opposite ends of each of the plurality of apertures 66 in a bipolar configuration. While each of the electrodes are heretofore described as being physically connected to the recording/stimulation unit 60, (e.g. via wire traces 58), it can be appreciated that the electrodes may be terminated at a wireless unit that could receive and transmit data signals between the electrodes and an external device, such as recording/stimulation unit 60, without deviating from the scope of the present invention.

In operation, rod 18 is inserted into intramedullary canal 74 of long bone 76 (e.g., a femur, a tibia or a humerus) of an amputated stump 75 using standard clinical techniques, FIG. 2. As hereinafter described, it is contemplated for intramedullary canal 74 of bone 76 to serve as a protected environment to house electrically active peripheral nerve 16 after extremity amputation. It is intended for the outer diameter of rod 18 to approximate the diameter or intramedullary canal 74 such that rod 18 fits snuggly in intramedullary canal 74 with minimal need for additional stabilization.

With rod 18 snuggly fit within intramedullary canal 74 of bone 76, peripheral nerve 16 is carefully exposed, isolated and cleaned by bluntly dissecting the musculature surrounding it. After being carefully isolated, peripheral nerve 16 is sharply transected at its most distal location, e.g. terminal end 26. In addition, peripheral nerve 16 is mobilized for several centimeters at a location sufficient to preserve adequate vascularity, while still allowing for adequate and tension-free mobilization of peripheral nerve 16 into intramedullary canal 74. Once peripheral nerve 16 has been adequately mobilized, nerve interface 50 is positioned on terminal end 26 of peripheral, nerve 16 such that electrodes 56 along inner surface 54 of pad 52 of nerve interface 50 engage the outer surface of peripheral nerve 16 in order to isolate the nerve impulses from peripheral nerve 16 located within intramedullary canal 74 and/or provide electrical stimulation thereto. Alternatively, in the event nerve interface 50 includes spike electrodes 62 projecting from inner surface 54 of pad 52, FIG. 5, spike electrodes 62 penetrate the outer surface of peripheral nerve 16 as nerve interface 50 is positioned on terminal end 26 of peripheral nerve 16 in order to isolate the nerve impulses from a variety of depths within peripheral nerve 16 on which neural interface 50 is received.

Upon positioning of nerve interface 50 on terminal end 26 of peripheral nerve 16, peripheral nerve 16 is, redirected into intramedullary canal 74 in bone 76. More specifically, a corticotomy is performed to form opening 80 in bone 76 at a location wherein a several centimeter segment of peripheral nerve 16 can easily be redirected in a tensionless manner through opening 80 in bone 76 and into intramedullary canal 74. Peripheral nerve 16 is anchored to bone 76 to provide stabilization and prevent retraction of peripheral nerve 16. For example, the epineurium of peripheral nerve 16 may be carefully stitched to the periosteum on the outer surface of bone 76 at the corticotomy site to provide the necessary stabilization and prevent retraction of peripheral nerve 16 from bone 76. Alternatively, it is contemplated to anchor peripheral nerve 16 to opening 80 in bone 76 with a microfabricated mechanical structure or by affixing peripheral nerve 16 to bone 76 with a biomaterial.

After being redirected into the intramedullary canal 74, peripheral nerve 16 is inserted into opening 32 in first end 29 of rod 18, FIG. 2, or opening 34 in rod 18, FIG. 1, such that peripheral nerve 16 and nerve interface 50 is positioned on terminal end 26 of peripheral nerve 16 are received in cavity 24 of rod 18. Wire traces 58 are routed within cavity 24 and the second ends of wire traces are operatively connected to recording/stimulation unit 60. In the depicted embodiment, recording/stimulation unit 60 is shown as a single, integral unit. However, individual recording and stimulation units are contemplated as being within the scope of the present invention. It is intended for recording/stimulation unit 60 to be retained in cavity 24 of rod 18. It can be appreciated that by providing neural interface 50 and recording/stimulation unit 60 within rod 18 in intramedullary canal 74 of bone 76, neural interface 50 and recording/stimulation unit 60 are shielded from surrounding muscle and confounding electromyographic cross-talk, protected from scar tissue formation, and stable during movement. The output of recording/stimulation unit 60 is operatively connected to connector 84 at prosthetic coupling 44. In order to interconnect prosthetic 14 to amputated stump 75, connection member 19 of prosthetic 14 is connected to prosthetic coupling 44, and hence, to the amputated stump 75 in any conventional manner. Connector 84 of ONI 10 is interconnected connector 17 of prosthetic 14 to electrically connect recording/stimulation unit 60 and controller 15. However, it is also contemplated to wirelessly connect recording/stimulation unit 60 and controller 15 in a conventional manner without deviating from the scope of the present invention. Alternatively, prosthetic 14 may be connected to stump 75 through other conventional means, such as a sleeve or harness. As such, recording/stimulation unit 60 and controller 15 would be wirelessly connected.

As is known, peripheral nerve 16 carries nerve impulses from the brain and spinal cord to the muscles of the now amputated limb, as well as, nerve impulses from peripheral sensory aspects back to the spinal cord and brain. Electrodes 56 (or spike electrodes 62) along inner surface 54 of pad 52 of nerve interface 50 isolate the nerve impulses from peripheral nerve 16 located within intramedullary canal 74. Electrodes 56 (or spike electrodes 62) are selected and designed to achieve maximized recording surface area and fidelity given the surface area, diameter and length of peripheral nerve 16 in cavity 24 of rod 18 and/or designed to maximize their electrical stimulation capabilities of the nerve interface. Analog signals corresponding to the nerve impulses sensed by electrodes 56 (or spike electrodes 62) are transmitted along wire traces 58 to recording/stimulation unit 60. Recording/stimulation unit 60 converts the analog signals to corresponding digital signals which are filtered. The filtered digital signals are transmitted to controller 15 within prosthetic 14. Controller 15 executes a predetermined algorithm so as to generate instructions on line 88 for mechanical drive system 89 that drives movement of prosthetic 14 in response to the nerve impulses from peripheral nerve 16 located within intramedullary canal 74 which were detected by electrodes 56 (or spike electrodes 62) of neural interface 50, FIG. 1.

In addition, it is contemplated for prosthetic 14 to include a plurality of sensors 91. The plurality of sensors 91 may take the form of pressure sensors, temperature sensors, position sensors, or the like for sensing various external factors acting on prosthetic 14. The signals generated by the plurality of sensors 91 are transmitted to controller 15. Controller 15 executes a predetermined algorithm to generate instructions on line 21 for recording/stimulation unit 60 such that recording/stimulation unit 60 provides electrical stimulation to peripheral nerve 16 via one or more desired electrodes 56 or 62. Alternatively, controller 15 may execute an electrical stimulation protocol, known to those skilled in the art, to cause recording/stimulation unit 60 to provide electrical stimulation to appropriate elements of peripheral nerve 16 via one or more desired electrodes. This could be done in a closed loop fashion Over time, it is contemplated for peripheral nerve 16 within intramedullary canal 74 to sprout nerve sprouts 40. As the nerve sprouts 40 extend from peripheral nerve 16, nerve sprouts 40 pass through apertures 66 in pad 52 of nerve interface 50 and through the plurality of fenestrations 36 adjacent first end 29 of rod 18 to the surrounding biological construct (i.e., bone 76 or the bone marrow of bone 76), FIG. 2. Hence, it is contemplated to provide neural interface 50 with sieve electrodes 70 about the plurality of apertures 66 extending through pad 52, FIG. 6, in conjunction with or instead of electrodes 56 or electrode spikes 62, to sense nerve impulses generated from nerve sprouts 40 extending from peripheral nerve 16. More specifically, as the nerve sprouts 40 extend from peripheral nerve 16, nerve sprouts 40 pass through apertures 66, and hence sieve electrodes 70, in pad 52 of nerve interface 50. Sieve electrodes 70 isolate the nerve impulses from nerve sprouts 40 of peripheral nerve 16 located within intramedullary canal 74. Analog signals corresponding to the nerve impulses sensed by sieve electrodes 70 are transmitted along wire traces 58 to recording/stimulation unit 60. Recording/stimulation unit 60 converts the analog signals to corresponding digital signals which are filtered. The filtered digital signals are transmitted to controller 15 within prosthetic 14. Controller 15 executes a predetermined algorithm so as to generate instructions on line 88 for mechanical drive system 89 that drives movement of prosthetic 14 in response to the nerve impulses from peripheral nerve 16 located within intramedullary canal 74 detected by sieve electrodes 70, FIG. 1.

In addition, controller 15 may execute a predetermined algorithm to generate instructions on line 21 for recording/stimulation unit 60 such that recording/stimulation unit 60 provides electrical stimulation to nerve sprouts 40 of peripheral nerve 16 via one or more desired sieve electrodes 70. Alternatively, controller 15 may execute an electrical stimulation protocol, known to those skilled in the art, to cause recording/stimulation unit 60 to provide electrical stimulation to appropriate nerve sprouts 40 of peripheral nerve 16 via one or more desired sieve electrodes 70. This could be done in a closed loop fashion.

Figure 8:
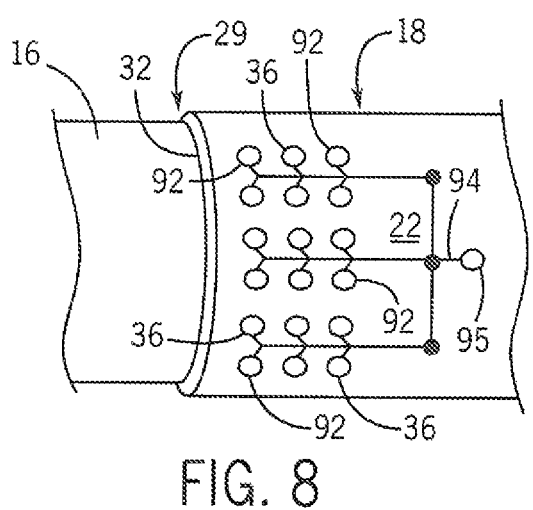
FIG. 8 is an isometric view showing a first end of a peripheral nerve received in a first end of an alternate rod for use with the osseointegrated neural interface of the present invention.

In a further embodiment, it is contemplated to replace neural interface 50 with a plurality of electrodes 92 about the outer periphery of rod 18 adjacent corresponding fenestrations 36 through rod 18, FIG. 8. Electrodes 92 are operatively connected to recording/stimulation unit 60 through lines 94 which may pass through opening 95 in rod 18 or wirelessly. After being redirected into the intramedullary canal 74, peripheral nerve 16 is inserted through one of opening 32 in first end 29 of rod 18 or opening 34 in rod 18 and into cavity 24 of rod 18, as heretofore described. The recording/stimulation unit 60 is operatively connected (physically or wirelessly) to connector 84 at prosthetic coupling 44. By way of example, connector 84 of ONI 10 may be interconnected to connector 17 of prosthetic 14 to electrically connect recording/stimulation unit 60 and controller 15. In order to interconnect prosthetic 14 to amputated stump 75, connection member 19 of prosthetic 14 is connected to prosthetic coupling 44, and hence, to the amputated stump 75 in any conventional manner.

As the nerve sprouts 40 extend from peripheral nerve 16, nerve sprouts 40 pass through the plurality of fenestrations 36 adjacent first end 29 of rod 18 to the surrounding biological construct (i.e., bone 76). Electrodes 92 positioned adjacent corresponding fenestrations 36 through rod 18 isolate the nerve impulses from nerve sprouts 40 of peripheral nerve 16 passing through fenestrations 36. Analog signals corresponding to the nerve impulses sensed by electrodes 92 are transmitted along lines 94 to recording/stimulation unit 60. Recording/stimulation unit 60 converts the analog signals to corresponding digital signals which are filtered. The filtered digital signals are transmitted to controller 15 within prosthetic 14. Controller 15 executes a predetermined algorithm so as to generate instructions on line 88 for a mechanical drive system that drives movement of prosthetic 14 in response to the nerve impulses from peripheral nerve 16 located within intramedullary canal 74 detected by electrodes 92.

In addition, controller 15 may execute a predetermined algorithm to generate instructions on line 21 for recording/stimulation unit 60 such that recording/stimulation unit 60 provides electrical stimulation to nerve sprouts 40 of peripheral nerve 16 via one or more desired electrodes 92. Alternatively, controller 15 may execute an electrical stimulation protocol, known to those skilled in the art, to cause recording/stimulation unit 60 to provide electrical stimulation to appropriate nerve sprouts 40 of peripheral nerve 16 via one or more desired electrodes 92. This could be done in a closed loop fashion.

Various modes of carrying out the invention, are contemplated as being within the scope of the following claims particularly pointing out and distinctly claiming the subject matter, which is regarded as the invention.

We claim:

1. An osseointegrated neural interface (ONI) for control of a prosthetic, comprising:
    an elongated, hollow rod having a first end receiveable in an intramedullary cavity of a bone, a second end operatively connected to the prosthetic and an inner surface defining a cavity;
    an electrode receiveable on a terminal end of a peripheral nerve and positionable within the cavity of the rod, the electrode configured to at least one of sense the neural signals generated by the peripheral nerve and stimulate the peripheral nerve; and
    an anchor operatively connectable to the bone for retaining the terminal end of the peripheral nerve within the bone.

2. The ONI of claim 1 wherein the electrode includes a plurality of openings therethrough, the plurality of openings adapted for allowing the passage of nerve sprouts from the peripheral nerve therethrough.

3. The ONI of claim 1 wherein the rod includes a plurality of fenestrations extending therethrough, the plurality of fenestrations adapted for allowing the passage of nerve sprouts from the peripheral nerve therethrough.

4. The ONI of claim 1 wherein the electrode includes a base and a plurality of spikes projecting therefrom, the spikes sensing the neural signals generated by the peripheral nerve.

5. The ONI of claim 1 wherein the electrode is operatively connected to a recording unit, the recording unit recording the neural signals from the peripheral nerve sensed by the electrode.

6. The ONI of claim 5 wherein the recording unit is receivable within the cavity of the rod.

7. The ONI of claim 5 further comprising a controller operatively connected to the recording unit, the controller controlling operation of the prosthetic in response to the neural signals recorded by the recording unit.

8. The ONI of claim 1 wherein the electrode is operatively connected to a stimulation unit, the stimulation unit transmitting signals to the electrode to stimulate the peripheral nerve.

9. The ONI of claim 8 wherein the stimulation unit is receivable within the cavity of the rod.

10. The ONI of claim 9 further comprising a controller operatively connected to the stimulation unit, the controller configured to control operation of the stimulation unit and the transmission of the signals to the electrode to stimulate the peripheral nerve.

11. A method of controlling a prosthetic, comprising the steps of:
    positioning a first end of an elongated, hollow rod within an intramedullary cavity of a bone, the rod having an inner surface defining a cavity;
    inserting a terminal end of a peripheral nerve within the intramedullary cavity of the bone;
    interconnecting a second end of the rod to the prosthetic;
    monitoring neural signals generated by a peripheral nerve; and
    transmitting the neural signals to a prosthetic controller, the prosthetic controller received within one of the rod, the intramedullary cavity of a bone and the prosthetic; and
    controlling movement of the prosthetic in response to the neural signals monitored.

12. The method of claim 11 comprising the additional step of anchoring the peripheral nerve to the bone.

13. The method of claim 11 further comprising the step of:
    positioning an electrode on a terminal end of the peripheral nerve, the electrode sensing the neural signals generated by the peripheral nerve.

14. The method of claim 13 comprising the additional step of configuring the electrode to allow nerve sprouts extending from the peripheral nerve to pass therethrough.

15. The method of claim 11 wherein the terminal end of a peripheral nerve is inserted within the cavity of the rod.

16. The method of claim 15 comprising the additional step of configuring the rod to allow nerve sprouts extending from the peripheral nerve to pass therethrough.

17. The method of claim 16 wherein the rod includes a plurality of fenestrations extending therethrough, the plurality of fenestrations adapted for allowing the passage of nerve sprouts from the peripheral nerve therethrough.

18. The method of claim 11 wherein the step of controlling movement of the prosthetic in response to the neural signals monitored includes the additional steps of:
    positioning an electrode about the peripheral nerve;
    recording the neural signals from the peripheral nerve sensed by the electrode; and
    controlling operation of the prosthetic in response to the neural signals recorded.

19. The method of claim 18 comprising the additional steps of:
    positioning a recording unit in the cavity in the rod; and
    operatively connecting the recording unit to the electrode.

20. The method of claim 19 comprising the additional step of:
  positioning the prosthetic controller in the prosthetic, the controller configured to control operation of the prosthetic in response to the neural signals recorded by the recording unit; and
  operatively connecting the prosthetic controller to the recording unit to receive the neural signals recorded by the recording unit.

21. The method of claim 11 comprising the additional steps of:
  sensing an external factor acting on the prosthetic; and
  stimulating the peripheral nerve in response to the external factor sensed.

22. The method of claim 21 comprising the additional steps of:
  positioning a sensor in the prosthetic for sensing the external factor; and
  operatively connecting a stimulation unit to the electrode.

23. The method of claim 22 comprising the additional step of positioning the prosthetic controller, operatively connected to the sensor and the stimulation unit, in the prosthetic, the prosthetic controller configured to transmit stimulation instructions to the stimulation unit in response to the external factor sensed by the sensor.

24. A method of controlling a prosthetic, comprising the steps of:
  positioning a first end of an elongated, hollow rod within an intramedullary cavity of a bone, the rod interconnected to the prosthetic and having an inner surface defining a cavity;
  inserting a terminal end of a peripheral nerve within the cavity of the rod;
  positioning an electrode on a terminal end of the peripheral nerve, the electrode sensing the neural signals generated by the peripheral nerve; and
  controlling movement of the prosthetic in response to the neural signals sensed.

25. The method of claim 24 comprising the additional step of anchoring the peripheral nerve to the bone.

26. The method of claim 25 comprising the additional step of configuring the electrode to allow nerve sprouts extending from the peripheral nerve to pass therethrough.

27. The method of claim 26 comprising the additional step of configuring the rod to allow nerve sprouts extending from the peripheral nerve to pass therethrough.

28. The method of claim 27 wherein the rod includes a plurality of fenestrations extending therethrough, the plurality of fenestrations adapted for allowing the passage of nerve sprouts from the peripheral nerve therethrough.

29. The method of claim 24 wherein the step of controlling movement of the prosthetic in response to the neural signals sensed includes the additional steps of:
  recording the neural signals from the peripheral nerve sensed by the electrode; and
  positioning a controller in the prosthetic, the controller configured to control operation of the prosthetic in response to the neural signals recorded by the recording unit.

30. The method of claim 24 comprising the additional steps of:
  positioning a recording unit in the cavity in the rod; and
  operatively connecting the recording unit to the electrode.

31. The method of claim 24 comprising the additional steps of:
  sensing an external factor acting on the prosthetic; and
  stimulating the peripheral nerve with the electrode in response to the external factor sensed.

32. The method of claim 31 comprising the additional steps of:
  positioning a sensor in the prosthetic for sensing the external factor; and
  operatively connecting a stimulation unit to the electrode.

33. The method of claim 32 comprising the additional step of positioning a controller operatively connected to the sensor and the stimulation unit in the prosthetic, the controller configured to transmit stimulation instructions to the stimulation unit in response to the external factor sensed by the sensor.

* * * * *